US012808835B2

(12) United States Patent
Wohltjen

(10) Patent No.: US 12,808,835 B2
(45) Date of Patent: Nov. 24, 2026

(54) EFFICACY-MONITORED SENSING SYSTEM AND METHOD

(71) Applicant: Enmet, LLC, Bowling Green, KY (US)

(72) Inventor: Henry Wohltjen, Bowling Green, KY (US)

( * ) Notice: Subject to any disclaimer, the term of this patent is extended or adjusted under 35 U.S.C. 154(b) by 286 days.

(21) Appl. No.: 18/234,775

(22) Filed: Aug. 16, 2023

(65) Prior Publication Data

US 2025/0060330 A1 Feb. 20, 2025

(51) Int. Cl.
*G01N 27/404* (2006.01)
*G01N 33/00* (2006.01)

(52) U.S. Cl.
CPC ..... *G01N 27/4045* (2013.01); *G01N 33/0027* (2013.01)

(58) Field of Classification Search
CPC ........... G01N 27/4045; G01N 33/0027; G01N 33/004
See application file for complete search history.

(56) References Cited

U.S. PATENT DOCUMENTS

| | | | | |
|---|---|---|---|---|
| 4,460,448 A | | 7/1984 | Wolcott | |
| 4,828,672 A | | 5/1989 | Lin | |
| 5,778,666 A | | 7/1998 | Cullen | |
| 6,454,923 B1 | | 9/2002 | Dodgson | |
| 6,948,352 B2 | | 9/2005 | Rabbett | |
| 7,073,368 B2 | | 7/2006 | Wood | |
| 7,174,766 B2 | | 2/2007 | Eickhoff | |
| 7,645,367 B2 | | 1/2010 | Tschuncky | |
| 7,704,356 B2 | * | 4/2010 | Kuhn | G01N 27/404 204/415 |
| 7,951,273 B2 | | 5/2011 | Caro | |
| 7,975,525 B2 | | 7/2011 | Bonne | |
| 8,306,665 B2 | | 11/2012 | Tsangaris | |
| 8,414,751 B2 | | 4/2013 | Nauber | |
| 8,888,987 B2 | | 11/2014 | Schattke | |
| 9,804,118 B2 | | 10/2017 | Sekiya | |
| 10,220,170 B2 | | 3/2019 | Tolmie | |
| 10,302,611 B2 | | 5/2019 | Holt | |
| 2002/0139419 A1 | * | 10/2002 | Flinchbaugh | F16K 31/04 137/557 |
| 2003/0145644 A1 | * | 8/2003 | Rabbett | G01N 33/0006 73/23.31 |
| 2004/0033414 A1 | * | 2/2004 | Rohrl | C07C 211/62 204/431 |
| 2005/0100478 A1 | | 5/2005 | Harvey | |
| 2017/0088957 A1 | | 3/2017 | Tschuncky | |
| 2019/0128833 A1 | | 5/2019 | Nakagaki | |
| 2020/0209183 A1 | | 7/2020 | Jian | |

FOREIGN PATENT DOCUMENTS

GB 2291189 A1 1/1996

OTHER PUBLICATIONS

Kroll, A.V. et al., "Electrochemical solid-state chlorine micro-generator for gas detector calibration" Sensors and Actuators B: Chemical, vol. 24, Issues 1-3 pp. 320-322.

* cited by examiner

*Primary Examiner* — C. Sun

(57) ABSTRACT

A system and method that support ascertainment of whether a sensing function is operative to determine the presence of a target substance and/or accurately quantitate such target substance, wherein a target substance generating function and a target substance sensing function are interconnected by a conduit through which a gas environment to be monitored or a test gas environment is measurably flowed.

13 Claims, 2 Drawing Sheets

EFFICACY-MONITORED SENSING SYSTEM AND METHOD

FIELD OF THE INVENTION

The present invention is in the area of efficacy-monitored exploration of a gaseous environment to detect whether or in what concentration a preselected target substance is present (including without limitation a vaporous substance as well as liquid or solid droplets or particles). This invention provides a system and method that support ascertainment of whether a sensing function is operative to determine the presence of the target substance and/or accurately quantitate such target substance. The result is that the sensing function can be corrected or (at least in some instances) the data obtained adjusted to compensate for variation in the function's sensitivity (due, for instance, to malfunction, "drift" or other deviation from the norm).

BACKGROUND OF THE INVENTION

The sensing of chemical vapors and gases is important to many endeavors such as environmental monitoring, process control, and hazardous atmosphere alarms. More specifically, toxic gas monitoring is critical for natural gas power plants, chemical processing, oil and gas production plants, and refrigeration facilities. Loss of containment of such hazardous gases can result in property loss through excessive corrosion, damage to the environment, and injury or death. Many of these toxic substances have poor physiological warning properties, meaning people can be overwhelmed by them before being aware of their presence. To protect workers and plant assets, as well as to avert harm to the environment and the public, organizations use gas detection systems. Toxic gas detection systems have a long history in the workplace and are mandated by law or corporate codes of practice or applied on a voluntary basis. Perhaps the most popular electrochemical sensor application today is for the measurement of carbon monoxide ("CO"). The technology is deployed in millions of homes and in tandem with many industrial devices for the purpose of warning of hazardous concentration levels of carbon monoxide in air breathed by humans.

A typical amperometric electrochemical gas sensor unit is depicted in FIG. 1. The sensor unit 1 has a "working electrode" 3 and a "counter electrode" 5 with a "reference electrode" 7 between, separated by a conductive electrolyte held in three wet filter components 9, 11 and 13 which are in communication with electrolyte reservoir 15. The electrolyte in the sensor unit contains water. The electrodes and electrolyte are retained in a cell by a membrane 17 (also called and referred to herein as a diffusion barrier) that allows ambient gases to diffuse into the cell while preventing the electrolyte from evaporating. Introduction of a gas into the cell causes the generation of an electrical current which is proportional in magnitude to the concentration of the gas.

By way of example, in the case of a CO sensor, the half-cell reactions are:

Working Electrode (WE) reaction: $CO+H_2O \rightarrow CO_2+2H++2e-$

Counter Electrode (CE) reaction: $\frac{1}{2}O_2+2H++2e- \rightarrow H_2O$

Therefore, when the sensor is in one mode of operation, CO is spontaneously oxidized to $CO_2$ at the working electrode with the coincident release of 2 electrons to create an electrical current which is easily measured using common signal conditioning circuitry.

The reverse phenomenon, i.e., electrolysis, is also known. Electrolysis causes gas generation as a result of passing an electrical current through electrodes immersed in an electrically conductive electrolyte. This technique has been used for more than a hundred years to generate many different gases.

Certain conventional developments involve the use of a sensor and a gas generator in combination. Thus, in UK Patent Publication 2,254,696A there is described a gas sensor deployed together with an electrochemical gas generating device in a closed package. The application of an electrical current to an electrolysis cell causes the production of hydrogen gas as a test substance that can be used to verify the operation of the combined gas sensor device. The amount of test gas produced is controlled by the charge delivered to the electrolysis cell. However, the technology in question is premised on the assumption that none of the generated test gas escapes from the combined generator/sensor enclosure (test-gas mass conservation). This is unfavorable because in practice the test gas can escape through a diffusion membrane that is provided to allow gases present in the ambient air to diffuse into the sensor. The problem arises insofar as the test gas escapes through the diffusion membrane. This leakage degrades test-gas mass conservation, and in turn the accuracy of detecting the test gas concentration. Moreover, unlike with the present invention (as discussed in subsequent sections hereof) no measurement of air flow is discussed.

Similarly, in U.S. Pat. No. 5,668,302 there is also discussed a gas sensor in combination with an electrochemical gas generator in a closed package. The U.S. Patent is focused on the incorporation of a "diffusion control" feature to allow a more direction application of the generated test gas to the sensing electrode of an electrochemical gas sensor. This supposedly reduces the amount of time needed for the test gas to reach the gas sensor and offers a quicker "bump-test" (a term commonly utilized to denote the exposure of a gas sensor to a known sample of the target for the purpose of checking that the sensor is performing as desired). Again, unlike with the present invention, no measurement of air flow is discussed.

Notwithstanding the state of sensor technology as discussed in the preceding paragraphs, the capacity to ascertain reliably—and without substantially disrupting system operation—a sensor's readiness to perform and continuing capacity to provide accurate information would be a significant advancement.

SUMMARY OF THE INVENTION

Accordingly, one object of the invention is to provide a system and method for determination of target-substance presence or concentration, wherein the determination is reliably accurate.

A further object of the invention is to provide a system and method for determining target-substance presence or concentration with reliable accuracy, wherein such result is obtained at relatively low cost.

Another objective of the invention is to provide a system and method as aforesaid wherein such reliably accurate and relatively low-cost determination is achieved while disruption of the smooth operation of target substance sensing is mitigated.

The foregoing objects, and additional ones as may be evident from this disclosure, are achieved by practice of the invention as hereinafter described.

Accordingly, one aspect of the invention is in an efficacy-monitored sensor system to test a subject gas environment for a preselected target substance, which sensor system comprises a sensor cell that includes a container having an internal cavity and located within the internal cavity a component capable of interacting with the preselected target substance and producing an output comprising or being convertible to an electrical current representative of the concentration of target substance detected by the sensor cell, said container further incorporating a membrane at least in part bounding the internal cavity, which membrane is capable of permitting passage of the subject gas environment including any preselected target substance, as well as a test gas environment including any preselected target substance, entrained therewith into the container's internal cavity;

an electrochemical generator cell for producing said preselected target substance that includes a container having an internal cavity, and located within the generator's internal cavity electrode components which are capable of interacting with one another as anode and cathode, said container being adapted for confining an electrolyte within said generator internal cavity, which electrolyte comprises a substance capable of interacting with a test gas environment or a constituent thereof to produce said preselected target substance, said container further incorporating a membrane capable of permitting passage into the generator cell's internal cavity of said test gas environment, and passage of preselected target substance out of the generator cell's internal cavity;

conduit providing a pathway for flow therealong of both said subject gas environment and said test gas environment including any preselected target substance entrained therewith, said conduit being interconnected at a first location with the electrochemical generator cell and at a second location with said sensor cell;

a source of said test gas environment which is capable of furnishing a flow of the test gas environment along said pathway and through the interconnection at the first location into said electrochemical generator cell's internal cavity, and further furnishing a flow of test gas environment suitable for entraining the preselected target substance passing out of said generator cell's internal cavity through the interconnection at said first location, thereby to transport said preselected target substance along said pathway to the second location and through the interconnection thereat into the internal cavity of the sensor cell;

a power source interconnected with said electrochemical generator cell's electrode components to induce between them an electrical current flow effective to bring about an interaction between the electrolyte substance and the test gas environment or constituent thereof which results in the production of said preselected target substance;

first circuitry interconnected with said power source and capable of directing said power source to induce an electrical current flow between the electrode components of said generator cell effective to bring about said interaction between the electrolyte substance and the test gas environment or constituent thereof which results in the production of said preselected target substance, whereby a first signal representative of the amount of current flow is produced;

a flow sensor located such that it is capable of intercepting the flow of test gas environment at said second location or past the second location in the direction of said flow, and second circuitry interconnected with said element to process the element's output and produce a second signal indicative of the test gas environment's flow; and third circuitry in electronic communication with said first circuitry and said second circuitry whereby to receive said first signal corresponding to current flow between the electrode components of the electrochemical gas generator and said second signal indicative of the test gas environment's flow, and capable of deriving therefrom whether any said preselected target substance is present or the concentration thereof.

In another aspect, the invention is in a method for efficacy-monitored testing of a subject gas environment for a preselected target substance by flowing the subject gas environment along a course running past a sensor cell, said course being in communication with the sensor cell, comprising at a time when said subject gas environment is not being tested, flowing a test gas environment from a source thereof along said course, and partially into an electrochemical generator cell having a confined space upstream of said sensor cell, in which space are located electrode components capable of interacting with one another as anode and cathode, and in which space is confined an electrolyte comprising a substance capable of interacting with the test gas environment or a constituent thereof to result in production of the preselected target substance, said space being bounded at least in part by a membrane capable of permitting passage of said test gas environment including any preselected target substance to enter into the space, and which is further capable of permitting passage of said preselected target substance out of said space;

applying to said electrode components an electric current effective to bring about an interaction between the electrolyte substance and said test gas environment or constituent thereof such that said preselected target substance is produced and at least in part exits such space;

entraining with the flow of test gas environment at least some of said preselected target substance exiting from the generator cell space;

flowing test gas environment along with the entrained preselected target substance further along said course to the sensor cell, whereby to introduce at least some of the entrained preselected target substance into the sensor cell such that said preselected target substance comes into contact with a component located in a confined space within the sensor cell and capable of interacting with at least some of the preselected target substance to produce an output comprising or being convertible to an electrical current flow representative of the concentration of target substance detected by the sensor cell;

measuring the current flow between said electrode components of the generator cell and producing a signal indicative of the amount of said current flow;

measuring the flow rate of the test gas environment including any entrained target gas substance at or past the location of said sensor cell and generating a signal indicative of said flow rate; and processing the signal indicative of said flow rate and the signal indicative of the amount of said current flow to derive therefrom whether any preselected target substance is present or the concentration thereof.

Practice of the invention confers substantial advantages. Thus, with the invention a test of the operativeness and/or accuracy of a sensing function can be monitored quickly, efficiently, without substantial disruption of the sensing operation, and at a time of the practitioner's choosing. Additionally, the incorporation of a flow-sensing function means that a determination of operability or accuracy of the sensing feature is not dependent on the prevention of any of the test gas environment's escape or leakage, which prevention is virtually impossible and hence difficult to achieve. Furthermore, the invention is especially helpful in making reliable determinations of target substances in situations where re-zeroing or other recalibration of the gas sensing feature is unduly disruptive, complicated or precluded by the sensor's inaccessibility. It follows that troublesome efforts to mitigate drift (such as re-zeroing or other recalibration operations) can be minimized or at least decreased without a meaningful sacrifice of efficiency. And, the invention is further desirable in that it involves elements already available (though repurposed); moreover, the invention can be implemented using commercially available components, which tends to conserve on cost.

DETAILED DESCRIPTION OF CERTAIN PREFERRED EMBODIMENTS

Figure 1:
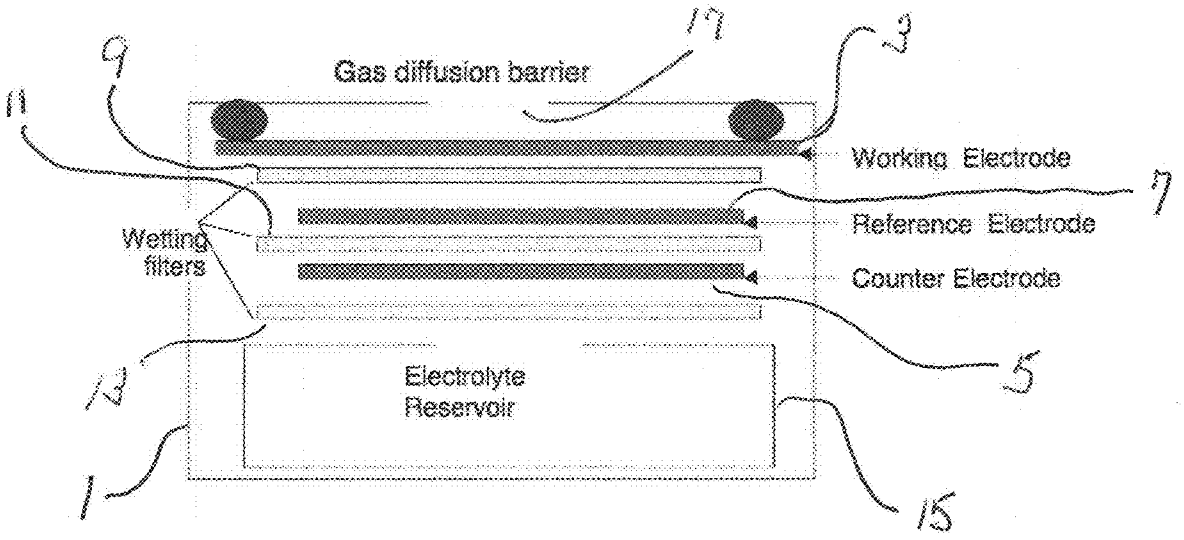
FIG. 1 is a schematic drawing of an amperometric electrochemical gas sensor configuration not involving the invention.

While involving sensor technology, the present invention is not concerned with the identification of unknown chemical vapors, or the rudimentary enablement of sensor detection of a target substance's presence or concentration when present. Instead, it is focused on reliability and accuracy in detection of a preselected target substance, especially when it is important to establish the operability or resistance to drift of the sensor function. Accordingly, the invention is in a discovery whereby target substance sensing operability and accuracy can be enabled efficiently and economically via deployment of a test gas environment against which actual performance can be conveniently evaluated vis-à-vis theoretical expectations. It should be noted that the precursor methodology for practice of the invention involves initially calibrating the sensing function. Calibration is important in order to establish a foundation for accurate measurement. So, while an important purpose of the invention is to mitigate the effects of drift or other corrupting influence in real time during the sensing operation, it is still basic to satisfactory sensing operations to begin from a well-founded and initially accurate determination of target substance concentration.

Operational Considerations

A significant aspect of this invention is the provision of a system and a method to verify the proper operation of target substance sensing technology and to support the re-zeroing or other re-calibration of the sensing technology through assessment of the technology's performance with a test gas environment whereby changes can be made to adjust for long-term deterioration in sensor sensitivity. This can be accomplished by the incorporation of (i) a feature whereby a gas environment flows along a course running past and in communication with a target substance generating function, and subsequently past and in communication with a sensing function, which functions are interconnected by a common pathway for gas environment flow, and (ii) a feature whereby the flow of the gas environment is measured at or past the place of said communication. As a consequence, a common flow path connects the target substance generating function, the target substance sensing function, and the flow measuring function.

The invention's working principle is that normal sensing operations are checked for efficacy via (i) preceding an interval of environmental monitoring with a determination of the sensing function's operability, and (ii) interspersing within such normal sensing operations intermittent generation and provision to the sensing function of a known concentration of target substance. The results with the target substance are compared with the results that are theoretically expected in order to ascertain whether there is any deviation from the ideal and (if so) by how much.

Therefore, the invention provides a system and method that confer a capability for verifying the operational readiness of a sensing function (sometimes referred to herein as "bump testing"), and also for re-zeroing or otherwise recalibrating a sensing function to compensate for drift, for instance, long-term drift. The foregoing is achieved through a feature, including a test zone, which can readily be brought "on-line" in the sensing operation to generate a known concentration of target substance to be sensed, such that the sensing function can be exposed to the deliberately generated target substance. As the presence and concentration of the target substance are already a theoretical "known", the performance of the sensing function in response to the target substance can be compared with the known and checked for capability and/or accuracy.

During normal operation, when the feed is the subject gas environment to be monitored, no current is applied to the electrode components of the test function and thus the generating function effectively has no (or at least only negligible) impact on the efficacy of the target substance sensing feature of the invention. The test function can readily be brought on-line (i.e., into effect) by instead subjecting the contents of the test zone, i.e., by applying across the electrode components of the test zone, an appropriate current, and using as the feed a test gas environment which comprises a species that interacts with the electrolyte to form the target substance. Accordingly, in consequence of applying the appropriate current the generating function is put into an active mode, whereby to cause production of the target substance. The test gas environment substituted into the flow arrangement, or a constituent thereof, interacts with the electrolyte (or some substance which is a part thereof) to result in the production, in a cavity housing the electrode components and the electrolyte, of the target substance in a concentration which can be theoretically calculated, and in parallel actually discerned, through the action of various other elements of the invention. The generated target substance or some part thereof exits the cavity and is carried as part of the test gas environment along a course which interfaces with the sensor function such that target substance can be detected if the function is operable. Furthermore, the test gas environment intersects with a flow measuring function such that the flow rate of the test gas environment including the entrained target substance can be ascertained. From this information, the concentration of target substance actually being presented to the sensing function can be calculated as a theoretical standard, and in turn compared with the actual performance of the sensing function to establish its operability and/or accuracy (or not) at testing. Therefore, key elements of this invention are the interconnection of the gas generating, gas sensing and flow measuring functions (the last of these being in the nature of a flow sensor, for instance). Data from the foregoing, when combined with the known mass delivery rate of the generator function, allow an accurate determination of the test gas concentration delivered by the generator function. Then, the performance of the gas sensor function when it is in the normal detection mode (and not the test mode) can be evaluated in terms of operability and accuracy.

Various features of the inventive efficacy-monitored sensor system and testing method are in and of themselves conventional. Thus, suitable technology is available separately and respectively for: (i) detection of the presence and/or amount of a target substance via measuring the electric current given off by a reaction of the target substance with another species; (ii) electrochemical generation of a known concentration (or mass) of target substance; (iii) measurement of flow rate at a location along a flow pathway; (iv) provision of a route along which a gas environment (whether or not including droplets or particles) can be furnished to a sensing function; and (v) electronic calculation of concentration and electronic comparison of same to actually detected concentration. Such devices and operations being individually well-known in the art, they are not shown and/or described beyond that degree of detail necessary for one of ordinary skill in the art to implement the invention's practice.

In a basic sense, the invention is well-suited to a threshold assessment of whether a sensing function is operable, i.e., whether it works at all to sense the presence of the target substance. As already indicated, such an assessment is called bump-testing. This can be carried out at the outset of sensing activities, or at any interim point, to make certain that the sensing function is operative to ascertain the presence of the preselected target substance in any sense.

Moreover, the invention is useful to determine if the sensing function is subject to drift or other degradation of accuracy. Preliminarily, sensor drift constitutes the emission of slowly varying signals correlated with changes in prevailing conditions, as well as aging of the sensor. The problem becomes especially acute when measurements are to be made over a long period of time. Uncompensated drift can significantly degrade measurement accuracy. Sensor drift can be compensated by periodically re-zeroing or otherwise recalibrating the sensor response to conform with one or more known characteristics of an appropriate sample. However, re-zeroing or other recalibration entails disruption of monitoring activity for substantial time intervals, not to mention that there are many scenarios requiring sensor-placement in locations that make it prohibitively difficult (or impossible) to perform intermittent re-zeroing and recalibration.

The invention disclosed herein thus provides a system and method having a two-fold effect. First, they provide for convenient bump testing of the gas sensing function at the outset of such activity. Second, they provide for detection of the onset of drift or other accuracy degradation, whereby to counter the drift or other degrading factor and reduce its influence on the accuracy of gas sensor measurement of concentration.

A central feature of the invention is inclusion of the following elements:

(1) an electrochemical generating function, embodied in an electrochemical cell, that serves as a place for generating known quantities of target substance through the process of electrolysis;

(2) an electrochemical sensing function, embodied in another electrochemical cell, that serves as a place for sensing the target substance;

(3) a flow sensing function, embodied in a flow sensor;

(4) a common flow path, embodied in a defining conduit that connects the electrochemical generating function/cell, the electrochemical gas sensing function/cell and the flow sensing function/cell.

Applying an appropriate electrical current causes the electrolyte and the test gas environment (or a constituent thereof) to behave such that the target substance is produced by an electrolysis reaction and diffuses out of the gas generating locus and into the stream of test gas environment flowing incident to the gas generating function. Additionally, while not inevitable, the redox potential of this reaction is in some instances similar to that required for evolution of one or more other substances due to a very significant competing reaction which exists to produce such one or more other substances that will also diffuse along with the target substance. The number of molecules of each of such aforementioned substances is directly related to the amount of electrical current applied to the electrolyte and test gas environment. Since it is straightforward to control the electrical current so delivered, it is straightforward to control the mass of target substance (and indeed such one or more other substances as well) generated.

Sensing Technology

As will be appreciated in light of the present disclosure, the invention is not only effective for electrochemical sensing, but also for a variety of non-electrochemical sensing devices and functions which in and of themselves are likewise conventional. Examples include, metal-oxide-semiconductor, photoionization, surface acoustic wave and thin film chemiresistor sensing technologies. Illustrative references are, respectively: Barsan, N., Koziej, D. and Weimar, U., "Metal oxide-based gas sensor research: How to?", Sensors and Actuators B: Chemical, Vol. 121 (1), 2007, pp. 18-35; Haag, W. R. and Wrenn, C.: "The PID Handbook—Theory and Applications of Direct-Reading Photoionization Detectors (PIDs)", $2^{nd}$. Ed., San Jose, CA: RAE Systems Inc. (2006); Ballantine, D., Jr., White, R., Martin, S., Ricco, A., Frye, G., Zellers, E., Wohltjen, H., "Acoustic Wave Sensors: Theory, Design, and Physico-Chemical Applications in Applications of Modern Acoustics", Academic Press; Cambridge, MA, USA; 1996; and Aswal, D., Gupta, S., "Science and Technology of Chemiresistor Gas Sensors", New Science Publishers, New York, 2007.

Even though the sensor technology varies from one approach to another, the basic operational approach remains the same. A sensor or sensing function is exposed during test intervals to a known concentration of preselected target substance. The output from the sensor/sensing function is compared with the output which is theoretically expected, to determine whether the actually sensed output varies from what was anticipated. In this manner, it can be ascertained whether a rectification of the sensing function's operability, or deviation-countering compensation—either by adjusting the sensing function's performance or the processing of its output—is necessary or desirable.

On the one hand, electrochemical sensors are nicely adapted for portable and fixed detection systems according to this invention. An electrochemical sensor is an electrochemical cell that employs a two- or three-electrode component arrangement (or in some embodiments even more such components) in which concentration measurements can be performed at steady or transient state. Frequently, electrochemical cells are amperometric. An amperometric device is one in which the current flowing through the system is related to the concentration of the desired species. When consisting of a three-electrode component system—the working, counter, and reference electrode components—an amperometric sensor operates at a fixed potential. Exposure of the cell to the substance of interest results in the production of two chemical reactions. These chemical processes produce a current that is directly proportional to gas concentration.

So, an electrochemical sensor is available for just about any target substance, and across a wide range of sensitivities, such as a highly accurate electrochemical CO sensor. Although they are designed to be as specific as possible, most electrochemical sensors will respond in some manner to substances other than the target substance. This is called cross-sensitivity and is a result of the sensor's electrolyte reacting with substances that are more chemically active than the target substance. In some cases, certain substances can even cause a reverse reaction in the sensor chemistry that can mask the presence of the target substance. The use of filters and bias voltage applied to the sensor during operation can reduce the effect of cross-sensitivity.

The subject environment (i.e., the one to be monitored), and the test environment, are more frequently gaseous in nature. However, in some embodiments either or both of such environments may contain droplets of liquid and/or particles of solid material. These droplets and particles are incidental to the operation of the invention, and as described elsewhere herein, are excluded from the zones where respectively target substance is generated and where it is sensed. For purposes hereof, the terms "test gas environment" and "test environment" shall be interchangeable in meaning and shall—except for dwell time in the zone where target substance is generated—be inclusive of environments in which are contained droplets or particles (or both) as aforesaid, as well as one or more gases. Alternatively, that environment can be made up of solely one or more gases. Similarly, for purposes hereof, the terms "subject gas environment" and "subject environment" shall be interchangeable in meaning and shall—except for dwell time in the zone where target substance is sensed—be inclusive of environments in which are contained droplets or particles (or both) as aforesaid, as well as one or more gases. Again, the subject gas environment can alternatively be made up solely of one or more gases.

It is generally the case that the target substance is a gas, but it can be accompanied by droplets or particles of materials that do not affect the operation of the invention to enable attainment of the stated objectives. Accordingly, the aforementioned species in some embodiments form a dispersion or emulsion of liquid or solid particles in the subject or test gas environment. A gas environment can be made up of a single gas or a gas mixture, i.e., a combination of multiple pure gases. Each gas constitutes atoms or molecules which are well-separated from one another and are not in rigid arrangement. So, when the target substance is a gas, it freely mixes with other components of the gas environment. The droplets and particles are preferably of size no more than 10 microns, emulsified or dispersed in the gas environment.

The advantages of electrochemical detection in harsh environments are well known: it is highly sensitive; consumes low power; has good specificity to target substances; enables a working pressure range proximate (e.g., within ten percent of) atmospheric pressure, thus mitigating the need for recalibration if used at high elevations; yields linear output of current-to-gas concentration to offer a real zero; and has a capacity for miniaturization. Since the detection mechanism involves the oxidation or reduction of the target substance, electrochemical sensors are optimal for substances which are electrochemically active, though it is possible to detect electrochemically inert gases indirectly if the gas interacts with another species in the sensor that then produces a response. Sensors for carbon dioxide are an example of this approach and they have been commercially available for several years.

Nevertheless—and in line with the present invention—electrochemical detection can be disadvantaged by various factors affecting the chemical reaction. The speed of reaction, for example, decreases with decreasing temperature. Sensor accuracy is also adversely affected by alkaline metals, which cause sensor drift, and by silicone vapors, which may coat the sensor surface and irreversibly inhibit sensitivity. Operation in low oxygen environments also alters sensor performance for sensors in which oxidation of the target substance takes place at the sensing electrode component.

One suitable alternative to electrochemical sensing is afforded by the electrical properties of semiconducting metal oxides. These sensors consist of a target-substance-sensitive resistive film, a platinum heater element, and an insulation medium. Such commercial gas sensors frequently make use of tin oxide or tungsten oxide combined with other oxides, catalysts, and dopants to increase the selectivity of the device. Such materials offer high sensitivity at lower reaction temperatures. Gas or other target substance molecules react on the metal oxide surface and associate into charged ions or complexes that alter the resistance of the film. This change is dependent on the physical properties of the metal oxide film as well as the morphology and geometric characteristics of the sensing layer and the temperature at which the reaction takes place. A heater circuit raises the temperature of the film to a range that yields optimal sensitivity and response time to the substance to be detected. Additionally, a pair of biased electrodes is embedded into the metal oxide to measure the change in resistance. This variation of the sensor that results from the interaction of the aforementioned molecules with the film is measured as a signal and is completely reversible. The signal is then converted to a target substance concentration.

Semiconductor sensors are advantageous because they are versatile and long-lived. Typical semiconductor sensors can detect a wide variety of gases and can be used in many different applications. Furthermore, they can do so over ten years or more, making their life expectancy among the longest of any detection technology available. Solid state sensors are also robust and have high tolerance to extreme ambient conditions and corrosive environments, making them a choice for monitoring target substances in hot dry climates.

The foregoing notwithstanding, solid-state sensors also have relative shortcomings. One is poor selectivity. Many solid-state sensors are affected by methyl mercaptan, chlorine gas, nitrogen oxide compounds, and other interference gases that alter the sensor reading. This makes the sensor output unreliable and could lead the instrument to trigger false alarms. Another drawback is high power consumption. Solid-state devices rely on a heater to regulate the temperature of the semiconductor film. High temperatures are required because the gas response (or gas sensitivity) of metal oxide films reaches a maximum temperature between 100 and 500 degrees C., depending on the composition of the film and the adsorption and desorption characteristics of the target substance on the metal oxide surface. The penalty for such high temperature is the need for a large and constant supply of energy. Moreover, solid state sensors are prone to baseline shifts over time. As a result, the sensor reading decreases on exposure to the same concentration of target substance, a phenomenon known as the "sleep effect".

On balance, an electrochemical cell is preferred for practice of the invention. The basic components of an electrochemical cell include a "working" electrode, an open "counter" electrode and optionally but frequently a "reference" electrode. These components are combined in a zone inside a housing with a liquid electrolyte. The sensor has a membrane and an optionally diffusion limiting orifice through which a gas environment (e.g., ambient air) interacts with the electrolyte. The gas environment (including target substance or its precursor in whatever form) diffuses through the membrane and comes in contact with the electrolyte. In an electrochemical sensor, an oxidation reaction results in current flow from the working electrode component to the counter electrode component, while a reduction reaction results in current flow in the opposite direction. The magnitude of this current flow is proportional to the amount of target substance present and is measured by an external electrochemical gas sensor circuit. This current is amplified, filtered, and processed to obtain a calibrated reading in engineering units. (Most electrochemical sensors output zero current when no target gas is present.) The known concentration of target substance theoretically produces a known current when fed to the sensor. If the sensor does not register a current or generates a current different from the one theoretically anticipated, the sensor is revealed to be inoperative or inaccurate.

Generating Technology

In contrast, concerning the target substance generating function, a known current is applied to the electrode components in the presence of a target substance precursor, to yield a known concentration of target substance. The target substance generating function involves an electrolytic cell wherein the input of electrical energy drives chemical reactions. The electrical energy induces redox reactions that store chemical energy. To do this, the electrolytic cell uses electrode components which comprise a positively charged anode and a negatively charge cathode. An anode is an electrode component which donates (or loses) electrons, and a cathode is an electrode component which accepts (or gains) electrons. In accordance with the invention, an electrolytic cell is subjected to current, i.e., a flow of electrons, originating from a power source. The current flows into the electrolytic cell and causes reduction at the cathode and oxidation at the anode. (Oxidation is the process of removing electrons from a compound; in reduction, electrons are added.) The transfer of electrons from the electrode component being oxidized to the one being reduced causes the generation of two new species, one of which is the target substance. The oxidation and reduction must occur together for the foregoing to take place. Oxidation or reduction cannot take place in isolation. It follows that, through a chemical reaction, target substance production is driven by application of a direct current producing the energy for the reaction to occur. The reaction would not occur without the electrical input because chemical reactions in electrolysis are not spontaneous.

Thus, a preferred embodiment of the invention comprises applying an appropriate electrical current to the generator electrode cell's components, which initiates an electrolysis reaction causing the electrolyte (or a substance therein) and the test gas environment (or a constituent thereof) to interact such that the target substance is produced and diffuses out of the gas generating locus and into the stream of test gas environment flowing incident to the gas generating function. Additionally, while not inevitable, the redox potential of this reaction is in some instances similar to that required for evolution of one or more other substances; this can be a very significant competing reaction which exists to produce such one or more other substances that will also diffuse along with the target substance.

Electrochemical technology provides important benefits in respect of the generating function too. One of them is a wide-ranging adaptability to practice of the invention. This is reflected in the variety of electrochemical features which can be deployed in connection with target substance generation. An array of electrode materials and material combinations are suitable as will be appreciated by one of ordinary skill in the art once in possession of the present disclosure. Similarly, an array of electrolyte compositions and/or bias voltages can be utilized to cause the generation of a range of different target substances, again as will be appreciated by one of ordinary skill in the art once in possession of the present disclosure.

As with the sensing function, the generating function typically involves amperometric measurements. The essential operation feature is the transfer of electrons between two electrode components immersed in a suitable electrolyte. A more complex and alternative arrangement involves the use of a three-electrode component cell, one of the electrode components serving as a reference. While the working electrode component is that at which the reaction of interest occurs, the reference electrode component provides a stable potential compared to the working electrode component. Inert conducting materials (e.g., platinum, graphite, Ag/AgCl, $Hg/Hg2Cl2$) are frequently used as the reference electrode component.

All Electrochemical

An especially favorable mode for practicing the invention is deployment of an electrochemical generating function and an electrochemical sensing function in tandem. On the one hand, one can produce an electric current through causing or energizing chemical reactions via an electrical power source, and on the other hand, produce an electrical current as a result of a chemical reaction. The electrochemical cell can be viewed as a convertor of energy. It converts electrical energy into chemical potential energy or chemical energy into electrical energy.

Preselected target substance is generated through application of a known current within the generator cell, the rate of which preselected target substance production is generated in direct proportion to the magnitude of the electrolysis current supplied to the generator cell. Preselected target substance diffuses out of the generator cell at a mass flow rate determined by the generator cell current. Additionally, the total volume of gas environment into which the preselected target substance is delivered can be determined using a flow rate sensor.

Concentration of target substance can be determined by knowing the rate at which the target substance is being generated (e.g., micrograms/minute) and the flow rate (e.g., liters/minute) of the test gas environment into which the target substance is disbursed. Dividing the mass flow rate of the target substance by the total flow rate provides a concentration (e.g., micrograms/liter) of the target substance. An electrochemical sensor receives the aforementioned target substance from the generator cell, then reports its presence and/or intermittently ascertains whether or not the sensor's output is in conformity with a value predicted theoretically from known conditions. If desirable the sensor cell's response can be adjusted to maintain high accuracy even when the sensor characteristics are changing with time.

In an especially preferred embodiment, the electrochemical sensor cell and electrochemical generator cell are of substantially the same, if not completely the same, configuration. In an extension of this concept, the same (or substantially the same) electrode component/electrolyte/membrane structure used in the electrochemical sensing function can be made to perform as an electrochemical generating function, if it is driven by an external electrical current. In the case of an amperometric electrochemical sensing function for CO in ambient air, the electrolyte will be in equilibrium with ambient humidity and carbon dioxide concentrations.

The invention is preferably practiced by utilization of electrochemical cells or zones in both the substance generating and substance sensing functions. It is even more advantageous to use the following basic design arrangement: electrode-components/electrolyte/membrane. That said, the electrode components can vary in number and configuration.

Thus, as indicated in preceding paragraphs, electrochemical cells are prominent in practice of the invention. Such cells are comprised of two essential elements:

The anode is the negative or reducing electrode component that releases electrons to the external circuit during an electrochemical reaction. The cathode is the oxidizing or positive electrode component that acquires electrons from the external circuit during the electrochemical reaction.

The electrolyte is the medium that provides an ion transport mechanism between the cathode and anode of a cell. Electrolytes are often thought of as liquids, such as water or other solvents, with dissolved salts, acids, or alkalis that are required for ionic conduction. It should, however, be noted that electrochemical cells can contain solid electrolytes that act as ionic conductors at room temperature.

Electrode Components

The electrode components preferably comprise at least two metallic or electronic conductors which when separated from each other and in contact with an electrolyte (such as a dissolved or fused ionic compound) allow the flow of current. Connection of the electrode components to a source of direct electrical current renders them respectively negatively charged and positively charged. Positive ions in the electrolyte migrate to the negative electrode component (cathode) and there combine with one or more electrons, losing part or all of their charge and becoming new ions having lower charge or neutral atoms or molecules; at the same time, negative ions migrate to the positive electrode (anode) and transfer one or more electrons to it, also becoming new ions or neutral particles. The overall effect of the two processes is the transfer of electrons from the negative ions to the positive ions, a chemical reaction (e.g., oxidation-reduction reaction). In the case of substances that generate energy (rather than consume it) when they react with each other, some or all of this energy can be converted to electricity if the reaction can be divided into an oxidation and a reduction that can be made to occur at separate electrode components. These processes create a driving force (a voltage or electrical potential) that causes electricity to flow through a circuit joining the two electrode components. Many other chemical combinations have been utilized in cells. The most desirable anode-cathode material combinations are those that result in a light-weight cell with high voltage and capacity.

In a three-electrode component cell a counter electrode component, also called a reference electrode component, is used only to make a connection to the electrolyte so that a current can be applied to the working electrode. The counter electrode is usually made of an inert material, such as a noble metal or graphite, to keep it from dissolving.

More specifically, there can be two, three or even more electrode components, as long as at least one acts as a cathode and at least one acts as an anode in respect of one another. Similarly, electrode component configuration can take any of a range of varied conventional designs, depending on which fits the application best. While its utilization in connection with the invention is innovative, in and of itself electrochemical cell technology is well-known.

Suitable cathode materials advantageously exhibit one or more of the following properties:

efficient oxidizing agent,
stable when in contact with electrolyte,
useful working voltage, and
metallic oxide nature.

The invention can be practiced with cathodic materials which include metals, graphite and metal oxides.

Metals suitable for cathodic deployment can be divided into three groups (i) platinum, platinum metals, nickel, and gold; (ii) copper, silver, iron, iron alloys including steel, aluminum, titanium, chromium, molybdenum, tungsten, bismuth, cobalt, nickel and nickel chromium steel; and (iii) mercury, palladium, cadmium, tin, zinc, tellurium, tin-lead alloys, and zinc-cadmium alloys. Oxides of such metals can also be utilized.

Graphite is a cathodic material which can readily be used for an electrode component. The graphite is a porous material. It is characterized by considerable ability to absorb or adsorb many substances. During oxidation of the graphite its specific surface area increases, and sorption ability becomes higher. The nature of the surface layer also changes due to formation on it of characteristic functional groups (e.g., hydroxide, carbinyl, carboxyl, peroxide, quinone) activating selectively chosen electrochemical processes. The invention can also be practiced with polymer-based and ceramic-based electrodes. A common CO sensor uses platinum black fixed to a porous PTFE membrane as electrode components.

Electrode component materials such as carbon, platinum, gold, silver, nickel, copper, dimensionally stable anions have been very popular because of their versatile potential window, low background current, low cost, chemical inertness, and suitability for various sensing and detection applications.

Metal oxides and other chemically modified electrode component materials can also be utilized. These result from a deliberate immobilization of a modified agent on the electrode component surface through chemical reactions, chemisorption, composition formation or polymer coating. Compared to conventional electrode materials, greater control of electrode characteristics and reactivity is achieved by surface modification, since the immobilization transfers physicochemical properties of the modifier to the electrode surface.

The cathode materials may include additional conductive material and electrolyte material. Suitable electroactive cathode materials include oxides and conducting carbon materials, such as acetylene black, carbon black, carbon nanotubes, and the like. Also useful are carbon derivative electrode materials which comprise pyrographite, glass-like carbon and carbon pastes.

Suitable anode materials include metals and their alloys, graphite and carbon-like materials, semi-conductive metal oxides and other semiconductors with a relatively high conductivity, characterized by a significant chemical resistance in aggressive environments. The preceding disclosure regarding graphite-containing cathode materials applies as well to anode materials. For example, the anode can be lithium metal, indium metal, nano-silicon composite material, silicon alloys, carbon (e.g., graphite), and combinations of these materials. Anode components can also comprise amorphous, modified and composite materials (both metallic and non-metallic) as well as porous and non-porous materials. Ceramic products can also be used as electrode materials, as can solid conductive polymers, microcrystalline and nanocrystalline materials.

As with cathode materials, chemically modified materials are also suitable. They are produced by way of immobilization of different non-organic and organic activators on any conductive substrate. Hetero- and isopoly-oxoacids and their salts, and even tungstic acid, can be used for modification of such materials as gold, tungsten, mercury, glass-like carbon, graphite and also platinum.

Electrolytes

Electrolytes suitable for practice of the invention advantageously exhibit one or more of the following properties:

- strong ionic conductivity,
- no electrical conductivity,
- non-reactivity with electrode materials,
- properties resistant to temperature fluctuations, and
- safe handling.

One of the most important qualities that an electrolyte possesses is an ability to support current flow. Electrochemical reactions always produce or consume ions at electrodes. But the electrolyte provides the pathway for ions to flow between and among electrodes in the cell to maintain charge balance. Ionic conductivity in electrolytes depends on two main factors: the concentration of free charge carriers and the ability of the charge carriers to move in an electric field. Electrolytes can be broadly considered in two groups: strong electrolytes and weak electrolytes. Strong electrolytes are normally fully dissociated into ions when dissolved, whereas weak electrolytes normally exist in a partially dissociated form such that some portion of the dissolved electrolyte exists in an unchanged form, usually a neutral molecule.

So, the electrolyte is usually a solution of water or other solvents in which ions are dissolved. Molten salts such as sodium chloride can also function as electrolytes. When driven by an external voltage applied to the electrode components, ions in the electrolyte are attracted to an electrode component with the opposite charge, where charge-transferring (also called faradaic or redox) reactions can take place. The electrical energy provided can produce a chemical reaction that would not otherwise occur spontaneously.

Electrolytes suitable for practice of the invention are substances that conduct electric current as a result of a dissociation into positively and negatively charged particles called ions. These migrate toward and ordinarily are discharged at the negative and positive terminals (cathode and anode) of an electric circuit, respectively. Typical electrolytes are acids, bases, and salts, which ionize when dissolved in a polar solvent such as water or alcohol. Many salts, such as sodium chloride, behave as electrolytes when melted in the absence of any solvent, and some such as silver iodide are electrolytes even in the solid state. While mineral acids are more commonly used, organic electrolytes are also useful in some instances.

Additionally, the invention can be practiced with a solid electrolyte for faster sensing capability and minimum maintenance. A suitable material is yttria-stabilized zirconia plate.

Some common electrolytes for aqueous electrochemistry are the alkali metal salts of nitrate, borate, halides, phosphate, phosphonates, carbonate, sulfate, and perchlorate. Concentrated solutions of strong Bronsted-Lowry acid (sulfuric acid, phosphoric acid or perchloric acid) or base (potassium hydroxide, sodium hydroxide or lithium hydroxide) are also acceptable electrolytes.

Membrane Technology

Once in possession of the invention, one of ordinary skill in the art will be able to devise the design of a membrane which provides diffusion control suitable for the practice of the invention. The design is keyed to what species it is desired reach the surfaces of the electrode components. A membrane is selected which has a porosity sufficiently great to allow passage of the species which need to enter or exit the generator zone or the sensor zone (as the case may be). The membrane preferably has a maximum pore size of 10 microns, though the maximum pore size can be less than 10 microns, all the way down to 0.5 microns. The membrane comprises a material or materials not disruptively interactive with the target substance, its precursor and other materials which are components of the subject and test gas environments. Polymer-based material is a practical and preferred choice for the membrane, e.g., Teflon, preferably disposable. The membrane can also be a film, more specifically a silicone film, such as a dimethylsilicone film.

For the invention to be effective, the membrane of the gas generating function includes openings that are of sufficient size that they can pass the test gas environment, including any constituent of the test gas environment which interacts with the electrolyte to produce target substance, along with the target substance itself. The openings, or at least a portion of them, are large enough that the intended species can migrate through the membrane. And, these same considerations pertain to the features of the membrane utilized for the sensing function, taking into account that the species involved in the sensing function include the components of the gas environment and the target substance.

Of course, the gas molecules or atoms of the gas environment—including gaseous target substance precursor and gaseous target substance per se—can cross the membrane through relatively small openings. It follows that in the frequently occurring event that there are no droplets or particles of interest in the practice of any particular embodiment of the invention, the openings of the membrane can be so small that the droplets or particles are excluded, i.e., filtered out.

Diffusion control offers a substantial advantage. Changing the membrane allows tailoring the sensor to a particular target substance concentration range. In addition, since the diffusion barrier is primarily mechanical, the calibration of electrochemical sensors tends to be more stable over time and so electrochemical sensor-based instruments often require less maintenance than some other detection technologies.

Electrical Current

The electrical current needed for provision to the cathode of the generator cell is derived from a suitable power source. Such power sources in and of themselves are well known to those of ordinary skill in the art. The power source is typically a generator or battery, which in either case is of sufficient capacity to supply enough current on command that the energy required to result in production of the target substance from its precursor is furnished. The power source is capable of being activated and deactivated as is appropriate to furnishing the requisite current to the target substance generating function for the time when the generating function is on-line (or for some part of that time). Note that the generating function is on-line at the point that its output commences being fed to the sensing function and the test gas environment commences being fed to the generating function.

Target Substances and Their Environment

The invention is well-suited to the accurate determination of the presence and concentration of unwanted, and in some cases toxic, target substances-substantially undistorted by the adverse effects of "drift" or other corrupting influences. Target substances of heightened interest are chemically reactive "fixed gases", e.g., hydrogen, carbon monoxide, ammonia, hydrogen sulfide, hydrogen cyanide, fluorine, phosgene and arsine. These species are more commonly detected with electrochemical technology, though other sensing technologies can also be suitable. Other target substances can also be detected, for instance, hydrocarbons, including alkanes, alkenes, alkynes and aromatics (examples are the chief components of petroleum and natural gas such as methane, ethane, propane, butane, isobutylene and other reducing gases); alcohols, aldehydes, ketones, acids, esters, ethers, and cyclic species, whether saturated or unsaturated, and whether or not containing heteroatoms. While such other target substances can also be detected with electrochemical technology, they are more commonly detected with one of the other sensing technologies. Mixtures of the aforementioned target substances or some of them are also detectable with the invention.

The environment being monitored, i.e., the subject environment, can be ambient air or some other prevailing mixture of substances streaming into or by the sensing function, introduced into the flow path of the sensing function. In various advantageous embodiments such introduction into the flow path amounts to propelling the subject environment into the flow path, for instance by the action of a fan or due to the application of pressure, including through the effect of a pressurized source such as a breathing air compressor or a pump. As will be clear from the instant disclosure, the test gas environment containing a precursor of the target substance can be ambient air, compressed air, or some other prevailing mixture of substances. The test gas environment can likewise be introduced into the flow path, which in accordance with the invention is in common communication with the generating function and sequentially the sensing function. Again, in various advantageous embodiments such introduction of the test gas environment into the flow path amounts to propelling the test gas environment into the flow path, for instance by the action of a fan or due to the application of pressure, including through the effect of a pressurized source such as a breathing air compressor or a pump. At least some of the target substance precursor finds its way into the generating function, and then at least some target substance produced via the generating function is transported to the sensing function by means of the test environment moving along the aforementioned common flow path. It is a highly important benefit of certain preferred embodiments of the invention that the utilization of cumbersome cylinders of compressed gas, as typically used to calibrate sensors, is eliminated.

Flow Sensing

The invention incorporates a flow sensing function to measure flow rate in the pathway through which is transported the test gas environment from the generator to the sensor. Thus, a highly important element of the invention is the interposition of a flow sensing function at a location which permits ascertainment of the rate of flow of the test gas environment stream at or past the location of communication between the sensing zone and the stream. In such regard, the direction of flow is from the source thereof to and beyond the sensing function. A location further along the direction of flow from any particular place is "downstream" of that place; a location spaced apart from a particular place in a direction counter to the aforementioned flow is "upstream" of that place.

As described in preceding passages hereof, the purpose of the flow sensing function is to measure the rate of flow of the test gas environment so information on that parameter can be utilized in calculations to derive the concentration of target substance as aforesaid. Typical flow sensing instrumentation can be adapted for use in practicing the invention once the disclosure herein is in hand. In any event, the instrumentation for implementing the flow sensing function is in and of itself known to one of ordinary skill in the art, once in possession of the invention as described herein.

By way of clarification, flow can be measured in volumetric or mass flow rates, with units such as liters per second or kilograms per second, respectively. These measurements are related to the material's density.

Of course, gases are compressible and change volume when placed under pressure, are heated or are cooled. A volume of gas under one set of pressure and temperature conditions is not equivalent to the same gas under different conditions. That said, gas mass flow rate can be directly measured, independent of pressure and temperature effects, with for instance ultrasonic flow meters, thermal mass flow meters, Coriolis mass flow meters or mass flow controllers.

A flow sensing instrument includes a primary flow element, i.e., a device inserted into the flowing fluid that produces a physical property that can be accurately related to flow. For example, an orifice plate flow element produces a pressure drop that is a function of the square of the volume rate of flow through the orifice. A vortex meter primary flow element produces a series of oscillations of pressure. Generally, the physical property generated by the primary flow element is more convenient to measure than the flow itself. The properties of the primary flow element, and the fidelity of the practical installation to the assumptions made in calibration, are critical factors in the accuracy of the flow measurement.

It is especially preferable to measure flow rate with electronic devices that can correct for varying pressure and temperature (i.e., density) conditions, non-linearities, and for the characteristics of the fluid. For instance:

- Magnetic flow meters, often called "mag meters" or "electromags", use a magnetic field applied to the metering tube, which results in a potential difference proportional to the flow velocity perpendicular to the flux lines.
- Alternatively, ultrasonic flow meters are useful, such as Doppler and transit time meters. While they both utilize ultrasound to make measurements and can be non-invasive (measure flow from outside the tube or other conduit, also called clamp-on device), they measure flow by very different methods. Ultrasonic transit time flow meters measure the difference of the transit time of ultrasonic pulses propagating in and against the direction of flow. The time difference is a measure for the average velocity of the flow along the path of the ultrasonic beam. On the other hand, ultrasonic Doppler flow meters measure the Doppler shift resulting from reflecting an ultrasonic beam off the particulates in flowing fluid. The frequency of the transmitted beam is affected by the movement of the particles; this frequency shift can be used to calculate the fluid velocity. For the Doppler principle to work, there must be a high enough density of sonically reflective materials such as solid particles or air bubbles suspended in the fluid.

A direct measurement of mass flow can be obtained in a Coriolis flow meter. Furthermore, a direct measure of the density of the fluid is obtained. Coriolis measurement can be very accurate irrespective of the type of gas (or droplet or particulate dispersion in gas) that is measured.

There are several other flow sensing options, such as: (i) ones that are pressure-based, wherein pressure is measured either by using laminar plates, an orifice, a nozzle, or a Venturi tube to create an artificial constriction, and then pressure loss of fluids is measured as they pass that constriction; or (ii) by measuring static and stagnation pressures to derive the dynamic pressure. Examples are a Venturi meter, an orifice plate, a Dall tube, a pilot tube, and a laminar resistance meter. Also suitable is a "variable area meter", which measures fluid flow by allowing the cross-sectional area of the device to vary in response to the flow, causing some measurable effect that indicates the rate. Other useful technologies are optical flow meters which use light to determine flow rate. Further choices are laser-based optical flow meters which measure the actual speed of particles, a property which is not dependent on thermal conductivity of gases, variations in gas flow or composition of gases. Another option is sonar flow meters, especially when a non-intrusive solution is desired. Sonar flow meters have the capacity of measuring the velocity of liquids or gases within a conduit from outside such conduit, and then leverage this velocity measurement into a flow rate by using the cross-sectional area of the pipe and the line pressure and temperature.

In an especially preferred embodiment of the invention, flow is measured by utilizing a thermal conductivity-based technology. A sufficient current is applied to a thermistor to cause it to heat up, and the hot thermistor is located in the gas flow channel whereby to measure its temperature dependent electrical resistance. The thermistor is cooled by the flowing gas in a way that is proportional to the gas flow rate, thereby producing a easily measured electrical signal that can be calibrated to the gas flow rate.

Control and Relevant Functions

The various operations, measurements, detections, and the like are controlled or otherwise implemented via utilization of appropriate circuitry to effect the desired control or implementation. More specifically, circuitry, such as a processor, commands that electrical current be relayed through one or more interconnections to the intended electrode component. The amount of such current is that gauged to be sufficient for causing the desired outcome, i.e., the transformation of a preselected precursor into the subject target substance. Accordingly, by way of illustration, the aforementioned circuitry (optionally including one or more adjunctive components, such as a transistor) triggers the reaction of the precursor (which is in the test environment) to react with the electrolyte or a component thereof to generate target substance, in accordance with the foregoing. At an advantageous time, the circuitry (e.g., processor) brings about communication between the source of the test environment and zone in which generation of target substance is carried out, and further the furnishing of electric current to the appropriate electrode component. Thereafter, the circuitry brings about a cessation of the furnishing of current and the interruption of communication between the aforementioned source of test environment and the generation zone.

Detection is effected by circuitry, such as one or more processors, that records and stores the electrical current values from the sensor in question, records and stores the flow rate values emanating from the flow sensing instrumentation, and calculates the concentration of target substance detected by the sensor instrumentation. Additionally, appropriate circuitry commands a switch-over from supply of the environment for analysis to the test environment containing a precursor of the target substance, and a commencement of the supply of the test environment with which is introduced a required precursor of the target substance. This is so that the precursor can be subjected to current from the power source (in the presence of the chosen electrolyte) and a known concentration of target substance generated for provision to the sensing function under testing.

The invention's versatility is manifest in the range of circuitry options which are suitable for utilization in its practice. Therefore, the invention can be implemented with digital circuitry or analog circuitry. The circuitry can be separated into modular units, on a task-by-task basis, or can be partially integrated so that—while certain portions dedicated to a specialized task are separately configured—other portions which are not task-specific can be interconnected with task-specific portions, so the non-specific portions can be multiple-use in nature. In a preferred embodiment, the circuitry or one or more portions thereof are packaged in a processor, which can be modular (by task) or multi-purpose.

The circuitry can be designed to apply one or more algorithms, acting in a unified manner along with the invention's other elements, to ascertain the concentration parameter ultimately sought. Accordingly, a microprocessor-based data analysis system can be used. The microprocessor is clocked by a timer for memory refreshing and other purposes. So, by way of example, data may be sampled by the microprocessor to effect detection of target substance concentration, comparison of the actual concentration with the theoretically anticipated concentration of target substance, and adjustment of the sensing function to compensate for any drift, derivation of or implementation of other conductance pattern recognition techniques, using well-known algorithms. It will be understood from the disclosure herein that different levels of current may need to be provided from the power source to result in the generation of different target substances. Like certain other parameters involved in practicing the invention, the current is varied from one level to another through use of the aforementioned control circuitry interconnected with the power source.

Other Features

The containers in which electrochemical and other reactions involved in the sensing and generating operations can be made of any suitable material or materials which are not disruptively reactive with any of the substances that are present, or which otherwise interfere with the sensing or generating operations (as the case may be). The same applies to the material(s) of which the conduit forming the pathway connecting the aforementioned source of environment to be analyzed or the test environment utilized for testing the sensing function, the generating function, and the flow sensing function. Additionally, the conduit is preferably made of material(s) appropriately flexible so that it can be conformed to the shape of the generating and sensing instrumentation and the configuration of the available space. Materials suitable for use to make the container and the conduit are for instance non-reactive plastics such as Teflon and non-reactive metals or alloys such as stainless steel.

Example

Figure 2:
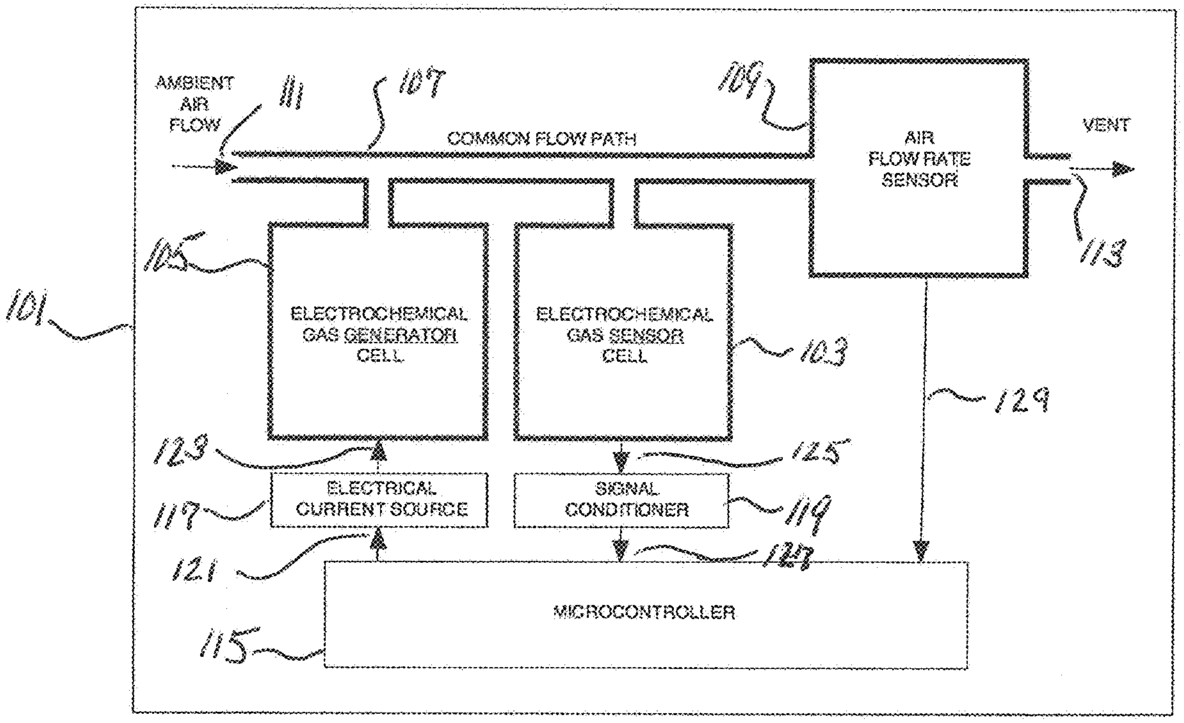
FIG. 2 is a schematic drawing of an efficacy-monitored electrochemical sensor system in accordance with the invention, suitable for practice of a method according to the invention.

In furtherance of providing an example of the invention, in FIG. 2 there is shown a sensor system 101 in accordance with the invention, depicted schematically. Thus, FIG. 2 is a block diagram of a system in accordance with the invention. A pair of "standard" electrochemical sensors is used, one as a gas sensing function or device 103, and the other as a gas generating function or device 105. The two devices are connected to a common flow path provided by tubing 107 that leads a normal gas stream being sampled to sensing device 103, where a target gas possibly in the stream can be detected. While not shown for the purpose of simplicity, the air to be monitored is provided from a pressurized source (e.g., a breathing air compressor) to move ambient air samples into the flow path of the system; alternatively, a small pump may for instance be utilized. When generator 105 is engaged, the flowing air stream serves to dilute gas released from the generator device, and to transport it to sensor device 103. Otherwise, the gas environment being monitored is moved from intake 111, along pathway 107, and (at least in part) into sensor 103. Thereafter, in either mode, the output from the sensor device 103 is carried along pathway 107 past flow rate sensor 109, which latter sensor measures such rate, and then on to vent 113.

Microcontroller 115 is interconnected with electrical current source 117 and signal conditioner 119. The generator is engaged by manually switching the feed from the gas to be monitored over to the test gas containing a precursor of the target substance such that the latter is fed into tubing 107 (or alternatively for example effecting the switch-over by electronic command from microcontroller 115 or another processor), and by commencing application of a preselected level of electric current for a desired amount of time, as directed by microcontroller 115. Due to the interaction of the generator's electrode components, resident electrolyte, and target substance precursor in the test gas environment, a mass flow rate of target substance exiting the generator cell can be calculated based on the direct proportionality of the target substance dispensed from the generator cell to the magnitude of current supplied. And the concentration of target substance dispensed from the generator cell into the flow stream of test gas environment, and in turn entering the sensor cell, can be derived by dividing the mass flow rate of target substance by the flow rate of the test gas environment stream in tubing 107, as measured by flow sensor 109.

Microcontroller 115 commands via circuitry 121 the application of the desired level of current from the current source 117 to the generator cell 105 via circuitry 123; additionally, microcontroller 115 receives information from sensor cell 103, and further from flow rate sensor 109. The output from sensor cell 103 is conducted through circuitry 105 to signal conditioner 119, wherein the output signal is modified (e.g., linearized, amplified, filtered and/or converted into a more advantageous form) through circuitry 127 to microcontroller 115. As well, the information from flow rate sensor 109 is conducted via circuitry 129 to microcontroller 115. Element 115 calculates the mass flow rate of target substance dispensed from generator cell 105, derives the concentration of target substance delivered to sensor cell 103, receives the processed output from sensor cell 103, and compares the concentration of target substance calculated with the concentration actually measured—in aid of revealing whether the sensor cell is working, and (if it is) whether the sensor cell is reading inaccurately and by how much.

It is an advantage of certain preferred embodiments of the invention that a mass-produced, commonly available, low-cost unit which is normally used as an electrochemical sensor cell can also function as the generating cell. This obviates the need for a more complex device structure and its associated costly manufacturing process. That the gas-permeable membranes of the two cells interface with a common flow path allows the target substance generated in one to be detected by the other.

In compliance with the statute, the invention has been described in language that enables its practice. It is to be understood, however, that the invention is not limited to the specific features shown and described. The invention, therefore, lies in any form or modification thereof within the proper scope of the appended claims appropriately interpreted in accordance with the doctrine of equivalents.

What is claimed is:

1. An efficacy-monitored sensor system to test a subject gas environment for a preselected target substance, which sensor system comprises a sensor cell that includes a container having an internal cavity and located within the internal cavity a component capable of interacting with the preselected target substance and producing an output comprising or being convertible to an electrical current representative of the concentration of target substance detected by the sensor cell, said container further incorporating a membrane at least in part bounding the internal cavity, which membrane is capable of permitting passage of the subject gas environment including the preselected target substance, as well as a test gas environment including said preselected target substance, entrained therewith into the container's internal cavity;

an electrochemical generator cell for producing said preselected target substance that includes a container having an internal cavity, and located within the generator's internal cavity electrode components which are capable of interacting with one another as anode and cathode, said container being adapted for confining an electrolyte within said generator internal cavity, which electrolyte comprises a substance capable of interacting with a test gas environment or a constituent thereof to produce said preselected target substance, said container further incorporating a membrane capable of permitting passage into the generator cell's internal cavity of said test gas environment, and passage of preselected target substance out of the generator cell's internal cavity;

conduit providing a pathway for flow therealong of both said subject gas environment and said test gas environment including said preselected target substance entrained therewith, said conduit being interconnected at a first location with the electrochemical generator cell and at a second location with said sensor cell;

a source of said test gas environment which is capable of furnishing a flow of the test gas environment along said pathway and through the interconnection at the first location into said electrochemical generator cell's internal cavity, and further furnishing the flow of test gas environment suitable for entraining the preselected target substance passing out of said generator cell's internal cavity through the interconnection at said first location, thereby to transport said preselected target substance along said pathway to the second location and through the interconnection thereat into the internal cavity of the sensor cell;

a power source interconnected with said electrochemical generator cell's electrode components to induce between them an electrical current flow effective to bring about an interaction between the electrolyte and the test gas environment or constituent thereof which results in the production of said preselected target substance;

first circuitry interconnected with said power source and configured to direct said power source to induce, at a time when the subject gas environment is not being flowed to the sensor cell, the electrical current flow between the electrode components of said generator cell effective to bring about said interaction between the electrolyte and the test gas environment or constituent thereof which results in the production of said preselected target substance, whereby a first signal representative of the amount of current flow is produced;

a flow sensor located such that it is capable of intercepting the flow of test gas environment at said second location or past the second location in the direction of said flow, and second circuitry interconnected with an element to process the element's output and produce a second signal indicative of the test gas environment's flow; and third circuitry in electronic communication with said first circuitry and said second circuitry whereby to receive said first signal corresponding to the current flow between the electrode components of the electrochemical gas generator and said second signal indicative of the test gas environment's flow, and configured to (i) derive from said first and second signals whether any said preselected target substance is present or (iii) calculate from said first and second signals the concentration of the preselected target substance actually present as well as to calculate a concentration of the preselected target substance anticipated to be present, and compare said actual concentration and said anticipated concentration.

2. A sensor system as defined in claim 1, wherein the sensor cell is an electrochemical device, a semiconductor device, a photoionization device, a surface acoustic wave device, or a thin-film chemiresistor device.

3. A sensor system as defined in claim 2, wherein the sensor cell is an electrochemical device.

4. A sensor system as defined in claim 1, wherein the sensor cell and the generator cell are electrochemical devices of substantially similar configuration.

5. A sensor system as defined in claim 1, wherein the flow sensor interfaces with the conduit downstream of the sensor cell's interface with the conduit.

6. A sensor system as defined in claim 1, which further comprises a reference electrode component interposed within the sensor cell, the generator cell, or both.

7. A sensor system as defined in claim 1, wherein the conduit is flexible tubing.

8. A sensor system as defined in claim 1, wherein the conduit is rigid tubing.

9. A sensor system as defined in claim 1, wherein the generator cell and sensor cell are each permanently interconnected with the conduit.

10. A sensor system as defined in claim 1, wherein the generator cell is detachably interconnected with the conduit.

11. A sensor system as defined in claim 1, wherein the sensor cell is detachably interconnected with the conduit.

12. A sensor system as defined in claim 1, wherein the membrane is formed of a polymer-based material.

13. A sensor system as defined in claim 1, wherein the target substance is carbon monoxide.

* * * * *